United States Patent [19]

Quadbeck-Seeger et al.

[11] 4,002,675

[45] Jan. 11, 1977

[54] MANUFACTURE OF 2-HYDROXY-NAPHTHALENE-3-CARBOXYLIC ACID

[75] Inventors: Hans-Juergen Quadbeck-Seeger, Ludwigshafen; Helmut Hoch, Wachenheim, both of Germany

[73] Assignee: BASF Aktiengesellschaft, Ludwigshafen (Rhine), Germany

[22] Filed: Feb. 6, 1975

[21] Appl. No.: 547,641

[30] Foreign Application Priority Data

Feb. 15, 1974 Germany .......................... 2407114

[52] U.S. Cl. .......................... 260/520 A; 260/345.3
[51] Int. Cl.$^2$ .......................... C07C 51/15
[58] Field of Search .......................... 260/520 A

[56] References Cited

UNITED STATES PATENTS 2,544,881  3/1951  Hodges et al. .......................... 260/520 A Primary Examiner—Norman Morgenstern
Attorney, Agent, or Firm—Johnston, Keil, Thompson & Shurtleff

[57] ABSTRACT

A process for the manufacture of 2-hydroxy-naphthalene-3-carboxylic acid by heating sodium β-naphtholate or a mixture of potassium β-naphtholate and sodium β-naphtholate with nitrogen compounds and/or polyphosphates containing at least 3 phosphorus atoms per molecule to a temperature of at least 180° C, reaction with carbon dioxide and subsequent reaction of the resulting salt with acid. The 2-hydroxy-naphthalene-3-carboxylic acid obtainable by the process of the invention is a starting material for the manufacture of dyes, a coupling component for dye lakes and for chrome dyes, and a developer for diazotizable dyes.

7 Claims, No Drawings

MANUFACTURE OF 2-HYDROXY-NAPHTHALENE-3-CARBOXYLIC ACID

This application discloses and claims subject matter described in German Patent Application P 24 07 114.5, filed Feb. 15, 1974, which is incorporated herein by reference.

The present invention relates to a process for the manufacture of 2-hydroxy-naphthalene-3-carboxylic acid by heating sodium β-naphtholate or a mixture of potassium β-naphtholate and sodium β-naphtholate with nitrogen compounds and/or polyphosphates containing at least 3 phosphorus atoms per molecule to a temperature of at least 180° C, reaction with carbon dioxide and subsequent reaction of the resulting salt with acid.

A process which has long been known for the manufacture of 2-hydroxy-naphthalene-3-carboxylic acid from β-naphthol is to convert β-naphthol to a sodium salt by reaction with sodium hydroxide solution and then to react the sodium salt with carbon dioxide at elevated temperatures and superatmospheric pressure to give the disodium salt of 2-hydroxy-naphthalene-3-carboxylic acid (BIOS Report No. 986, pages 234 et seq.; Ullmanns Encyklopaedie der technischen Chemie, Vol. 12, pages 606 et seq.). This process is unsatisfactory as it requires special equipment and entails high operating costs and energy costs. One of the principal difficulties of the process is that the sodium β-naphtholate must be dehydrated rapidly and completely before the carboxylation reaction. Even small amounts of water present during the carboxylation reaction reduce the yield of the disodium salt of 2-hydroxy-naphthalene-3-carboxylic acid. Drying the sodium β-naphtholate is difficult and lengthy. Since the sodium β-naphtholate is a solid and heat transfer is therefore poor, even carefully controlled heating and mixing of the naphtholate — which requires much time and therefore entails high costs — may not avoid local over-heating of the solid salt, causing it to decompose.

In order to improve the process, modifications have been developed. U.S. Pat. No. 2,132,357 discloses the reaction of sodium naphtholate in the presence of pyridine and its homologs. The apparatus must be made of nickel since iron vessels corrode and the iron compounds thus formed considerably assist the formation of the by-product naphthoxanthone. According to the disclosures of the above patent, the ready solubility of carbon dioxide in the solvent used is an important precondition for rapid carboxylation. The disadvantages of this process, particularly in industrial operation, are the objectionable odor and the toxicity of the solvents. When the naphtholate is heated, a large proportion of the solvent distils as an azeotrope with water and is lost from the reaction. Recovery of the solvent is difficult and expensive and solvent residues in the effluent cause environmental problems.

U.S. Pat. No. 2,132,356 discloses the use of cyclic ethers such as dioxane as solvents for the reaction. As in the case of pyridine, the apparatus cannot be constructed of iron. Since the ethers used are also substantially lost from the reaction together with water, the difficulties referred to above again arise during working up. The reaction must be carried out under high pressure. Since dioxane and its derivatives can contain peroxides as by-products, the safety of the process presents problems.

U.S. Pat. No. 1,503,984 discloses paraffin waxes and paraffin oils as the reaction medium; these materials retard the reaction and are difficult to recover. Particularly on an industrial scale, the process is involved and uneconomical. In the process described in British Pat. No. 638,196, dialkyl ketones are used. To obtain a solution, large amounts of solvent must be used, entailing high costs of materials and a low space-time yield.

German Published Application 2,132,296 discloses diphenyl, diphenyl oxide and alkylnaphthalenes with alkyl groups of 1 to 4 carbon atoms as the reaction medium. The solvents are volatile in steam and accordingly the above difficulties in working up, recovery of the solvent, and contamination of effluent, again arise. Compared to other solvents, alkylnaphthalenes are difficult to obtain and comparatively uneconomical.

In all these processes, but especially those which do not employ solvents, an unsatisfactorily large proportion of by-products is obtained, in the form of condensation products of β-naphthol and of resinous polymers of β-naphthol. The 2-hydroxy-naphthalene-1-carboxylic acid formed as an intermediate in the manufacture of the 3-carboxylic acid can undergo rearrangement to dibenzoxanthone and the basic naphthol can thus become unavailable either for recovery or for reaction to 2-hydroxy-naphthalene-3-carboxylic acid:

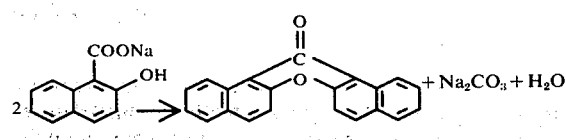

Particularly on an industrial scale, the formation of by-products thus continuously consumes β-naphthol and lowers the yield of end product. The removal of xanthone and the resins is expensive and in most cases requires additional purification steps.

It is an object of the present invention to provide a new process for the simpler and more economical manufacture of 2-hydroxy-naphthalene-3-carboxylic acid in good yield and improved purity and with a better space-time yield.

We have found that 2-hydroxy-naphthalene-3-carboxylic acid is obtained advantageously by reaction of sodium β-naphtholate with carbon dioxide at elevated temperature by a process wherein sodium β-naphtholate or a mixture of sodium β-naphtholate and potassium β-naphtholate is heated, in a first stage, in the presence of nitrogen compounds of the formula

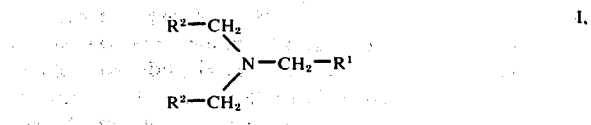

wherein R¹ is carboxyl, carboxylate or the radical

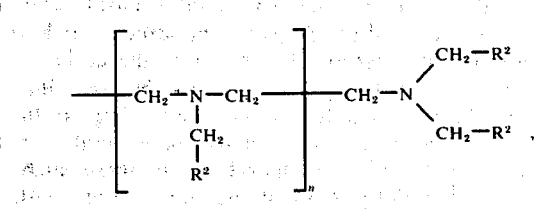

the radicals $R^2$ are identical or different and each is carboxyl, carboxylate or —$CH_2OH$, and $n$ is an integer including 0, and/or polyphosphates containing at least 3 phosphorus atoms per molecule, to a temperature of at least 180° C and is reacted, in a second stage, with carbon dioxide at the above temperature, and the resulting salt of 2-hydroxy-naphthalene-3-carboxylic acid is then converted to 2-hydroxy-naphthalene-3-carboxylic acid by addition of an acid.

The reaction can be represented by the following equations:

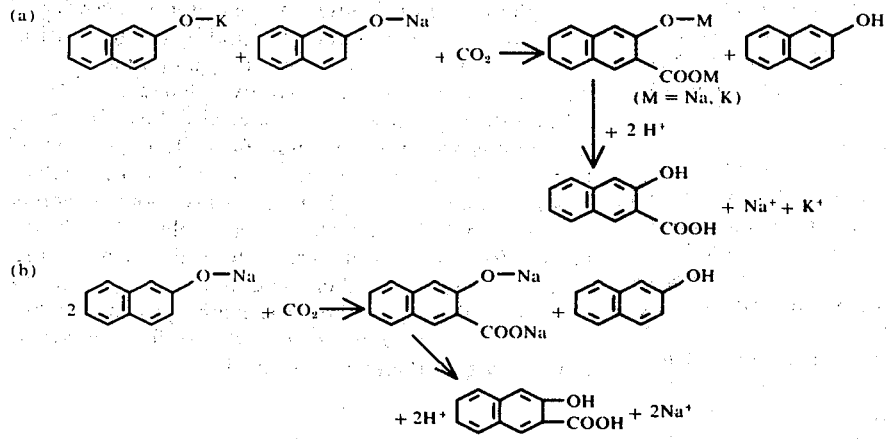

Compared to the known processes, the process according to the invention gives 2-hydroxy-naphthalene-3-carboxylic acid more simply and more economically, in good yield and improved purity and with improved space-time yield. When the naphtholates are heated, the dehydration takes place substantially more easily and more rapidly. As compared to processes which use solvents, the present process is more economical and does not require expensive apparatus for recovery of the solvent. Since the process does not use toxic or readily flammable solvents, the related problems of effluent contamination and protection of the health of operatives do not arise, and the problem poses less environmental problems. Furthermore, iron can be used for the construction of the apparatus without a noticeably increased formation of by-products. The plants can be operated reliably and simply, particularly on an industrial scale. The formation of by-products such as xanthones, condensation products of naphthol or polymeric resins of high molecular weight is substantially reduced. The proportion of by-products can, e.g., be lowered from 15 to 32 mole percent to 10 to 14 mole percent, based on naphthol starting material.

If mixtures of sodium β-naphtholate and potassium β-naphtholate are used, the normal dehydration time in the conventional process can be reduced to as little as one-tenth. The conventional processes which do not use solvents furthermore give hard reaction mixtures, which are difficult to digest, at the end of the first stage, and in industrial operation these mixtures must be comminuted and ground using special equipment, such as crushers or mills, before proceeding to the carboxylation stage; when using a mixture of the two alkali metal naphtholates in the process according to the invention, viscous or mobile melts are generally obtained, depending on the temperature, and these can be carboxylated directly. Correspondingly, energy costs and material costs are lowered compared to those according to the state of the art, and less personnel is required. Heat transfer in the reaction mixture of the 1st stage according to the invention is better and there is therefore no significant local overheating of the solid salt and hardly any decomposition which reduces the yield. The treatment of mobile melts with a gas is also easier than the treatment of solids. In the conventional processes, the β-naphthol formed increases the sticking-together and caking of the reaction mixture. In contrast, β-naphthol can easily be removed from the melts according to the invention by distillation or by stripping with a recycled stream of carbon dioxide.

The nitrogen compounds I and/or polyphosphates used as inhibitors of the formation of by-products are suitably employed in amounts of from 0.001 to 0.1 mole, preferably of from 0.005 to 0.01 mole, per mole of the naphtholate starting material. Preferred inhibitors are nitrogen compounds of the formula I, wherein $R^1$ is carboxyl, the radical

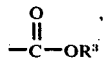

in which $R^3$ is half an alkaline earth metal atom, suitably a magnesium atom or calcium atom, or preferably, an alkali metal atom, especially a sodium atom or potassium atom, or the radical

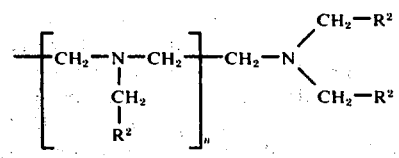

the radicals $R^2$ are identical or different and each carboxyl, the radical

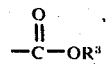

in which $R^3$ is half an alkaline earth metal atom, suitably a magnesium atom or calcium atom, or preferably an alkali metal atom, especially a sodium atom or potassium atom, or the radical —$CH_2OH$ and $n$ is 0, 1 or 2, and/or polyphosphates containing at least 3, preferably at least 4, and in particular at least 10, phosphorus atoms per molecule.

The polyphosphates can have a chain structure and be, preferably, tripolyphosphate or polyphosphates of the formula $Me_{m+2}[P_mO_{3m+1}]$ (wherein $m$ is an integer and Me is a metal atom) or a ring structure and can be, preferably, trimetaphosphate and tetrametaphosphate (Fleitmann's salts), or can simultaneously have a ring structure and a chain structure and be, preferably, isometaphosphates or ultraphosphates, or can have a chain structure with branches and be, preferably, isopolyphosphates. An oxide ratio $MeO + H_2O/P_2O_5$ of from 1 to 1.67 is preferred.

The polyphosphates can be used in the form of the salts, preferably of the alkali metal salts and alkaline earth metal salts, or of the partially hydrolyzed salts or of the acids on which they are based, and these compounds can be free from water of crystallization or be hydrates. Preferred metal cations of the polyphosphates are above all potassium and especially sodium and, as a second choice, calcium and magnesium. Regarding the definition and manufacture of polyphosphates, reference may be made to Ullmanns Encyklopaedie der technischen Chemie, Vol. 13, pages 540 to 559.

Examples of polyphosphates which can be used are: pentasodium triphosphate, sodium trimetaphosphate, sodium tetrametaphosphate, sodium hexametaphosphate, Maddrell's salt, sodium metaphosphates with 16 to 33 $NaPO_3$ units, sodium metaphosphates with 36 to 80 $NaPO_3$ units, sodium metaphosphates with 80 to 2,800 $NaPO_3$ units, Graham's salt, Kurrol's salt, high molecular weight potassium polyphosphate $(KPO_3)_x$ ($x$ = from 400 to 20,000), and appropriate mixtures.

Examples of suitable nitrogen compounds I are: nitrilotriacetic acid, ethylenediaminetetracetic acid, diethylenetriaminepentaacetic acid and appropriate monosodium, disodium, trisodium, monopotassium, dipotassium and tripotassium salts, the tetrasodium salt and tetrapotassium salt of ethylenediaminetetraacetic acid, the pentasodium salt, the tetrasodium salt, the pentapotassium salt and the tetrapotassium salt of diethylenetriaminepentaacetic acid, triethylenetetraminehexaacetic acid and its salts with 1 to 6 sodium cations or 1 to 6 potassium cations; triethanolamine, ethylenediamino-N-tetraethanol, diethylenetriaminopentaethanol and N-$\beta$-hydroxyethyl derivatives of the above acids in which, depending on the number of carboxymethyl groups present on the nitrogen atoms, 1, 2, 3, 4 or 5 of these groups are replaced by a $\beta$-hydroxyethyl group, and also appropriate sodium salts and potassium salts of the above N-$\beta$-hydroxyethyl-N-carboxymethyl compounds, in which one or more, or all, of the carboxyl groups present are in the form of sodium carboxylate or potassium carboxylate groups.

The naphtholates can be used as pure compounds; however, it is preferred to combine the manufacture of the naphtholates and the first stage of the process according to the invention and thus to carry out a three-stage single-vessel process, preferably with all stages being carried out in the presence of the inhibitor. The naphtholates can be manufactured in accordance with one of the conventional processes of manufacture of naphthol using sodium compounds or potassium compounds such as sodium carbonate, potassium carbonate, potassium hydroxide or sodium hydroxide to form the salt (Ullmanns Encyklopaedie der technischen Chemie, Vol. 12, pages 603 and 604). The $\beta$-naphthol is preferably dissolved in sodium hydroxide solution or in a mixture of sodium hydroxide solution and potassium hydroxide solution. The resulting solution or suspension of $\beta$-naphtholate is heated and used directly for the carboxylation reaction. The inhibitor, which is suitably in the form of an aqueous solution, preferably of from 30 to 50 percent strength by weight, can be added to the mixture of alkali metal hydroxide solution and $\beta$-naphthol from the start, separately or together with the alkali metal hydroxide solution or with the naphthol; however, it is also possible first to produce the naphtholate and then to add the inhibitor, before carrying out the heating required by the first stage of the process. If an acid is used as the inhibitor, the amount of alkali metal hydroxide solution is preferably increased by the amount required to neutralize this acid. The naphtholate can be manufactured under atmospheric or superatmospheric pressure, continuously or batchwise. The mixture from the manufacture of the sodium naphtholate, which is fed to the first stage of the reaction according to the invention, preferably contains the inhibitor and a total amount of sodium which, calculated as sodium hydroxide, corresponds to the stoichiometric amount, based on total naphthol in the mixture. If desired, the starting mixture can however also contain an excess of naphthol, for example of up to 10% by weight over the stoichiometric amount, based on the total amount of sodium (calculated as sodium hydroxide). A further possibility is to heat $\beta$-naphthol and aqueous sodium hydroxide solution to the reaction temperature, if appropriate under an inert gas such as nitrogen.

Where naphtholate mixtures are to be used, it is possible to produce the two naphtholates separately from one another by the above method and to combine the reaction mixtures obtained; however, a more suitable method is to produce the naphtholate mixture by a conjoint reaction. In general, the mixtures of alkali metal naphtholates contain from 0.02 to 0.5, preferably from 0.02 to 0.2, mole of potassium $\beta$-naphtholate per mole of sodium $\beta$-naphtholate; correspondingly, suitable molar ratios of potassium hydroxide to sodium hydroxide to be used for the manufacture of the starting materials are from 0.02 to 0.5:1, preferably from 0.02 to 0.2:1. The naphtholates can be produced at atmospheric or superatmospheric pressure, continuously or batchwise. The mixture from the production of the naphtholates which is fed to the first stage of the reaction according to the invention advantageously contains a total amount of sodium and potassium, calculated as sodium hydroxide and potassium hydroxide, which corresponds to the stoichiometric amount, based on total naphthol in the mixture. If desired, the starting mixture can however also contain an excess of naphthol, for example of up to 10% by weight over the stoichiometric amount, based on the total amount of alkali metal (calculated as the alkali metal hydroxide). A further possibility is to heat $\beta$-naphthol and aqueous alkali metal hydroxide solution to the reaction temperature, if appropriate under an inert gas such as nitrogen.

In the first stage of the reaction, the starting mixture is heated, at atmospheric or superatmospheric pressure, continuously or batchwise, to a temperature of at least 180° C, preferably of from 200° to 280° C and especially of from 240° to 265° C. The second stage of the reaction, the carboxylation, is also carried out under these temperature and pressure conditions, continuously or batchwise. On heating the starting mixture, e.g. for from 30 to 60 minutes, water distils off. The carboxylation is suitably carried out under pressure, preferably of from 2 to 50 atmospheres and especially of from 3 to 10 atmospheres, with an amount of carbon dioxide of from 0.5 to 10 moles, preferably of from 0.5 to 2 moles, based on naphtholate. The carboxylation reaction time is preferably from 1 to 4 hours and the end product is then isolated by customary methods. E.g., it is possible to cool the mixture and to introduce the suspension of the disodium salt of 2-hydroxy-3-naphthoic acid into water, or to distil off the entire amount of β-naphthol in vacuo and dissolve the residue in water at about from 90° to 100° C. The β-naphthol can also be stripped from the reaction mixture by means of the stream of carbon dioxide, which is preferably recycled. E.g., carbon dioxide is forced into the melt until the absorption of carbon dioxide subsides; the β-naphthol liberated is then distilled off by applying a vacuum and the residual melt is again carboxylated. These operations are repeated until no further carbon dioxide is absorbed and no further β-naphthol distils off, which is generally the case after from 2 to 4 carboxylations alternating with from 2 to 3 distillations of the β-naphthol formed. Acid is now added to the aqueous mixture to obtain the free carboxylic acid; a wide range of acids, and of methods of converting a salt into the corresponding acid, can be employed. Preferably, the pH of the aqueous mixture which contains the disodium salt of 2-hydroxy-naphthalene-3-carboxylic acid together with small amounts of sodium β-naphtholate is brought to about 5 with aqueous hydrochloric acid (e.g. of from 5 to 35% strength by weight) at from 60° to 70° C, and the β-naphthol which precipitates is filtered off, e.g., on a filter press. The aqueous phase which has been freed from the β-naphthol by filtration is then preferably acidified to pH about 3 with aqueous hydrochloric acid (for example of from 5 to 35% strength by weight) at from 85° to 95° C, stirred for from 5 to 15 minutes and then cooled, e.g. to 50° C, and filtered. Small amounts of 2-hydroxy-naphthalene-6-carboxylic acid present as an impurity in the 2-hydroxy-naphthalene-3-carboxylic acid can easily be removed because of the much greater solubility of the former in hot water. The isomer can be recovered from the wash water by cooling.

2-Hydroxy-naphthalene-3-carboxylic acid, manufactured by the process of the invention, is a valuable starting material for the manufacture of dyes and a coupling component for dyes for making lakes and for chrome dyes, and a developer for diazotizable dyes. Its uses are described in the publications mentioned above, especially in Ullmann, Vol. 12, page 609.

The parts in the Examples are parts by weight.

EXAMPLE 1

An autoclave with stirrer is charged with 1,240 parts of β-naphthol, 608 parts of aqueous sodium hydroxide solution (50% strength by weight), 27 parts of aqueous potassium hydroxide solution (85% strength by weight) and 6 parts of the trisodium salt of nitrilotriacetic acid (dissolved in 15 parts of water). The charge is mixed thoroughly under nitrogen, heated to an internal temperature of 260° C and maintained thereat for 30 minutes, after which dehydration is practically complete. The carboxylation is carried out at 260° C with dry carbon dioxide at 7 atmospheres pressure, and the absorption of $CO_2$ is followed by means of a gas meter. When the absorption has ceased, β-naphthol is distilled off under 20 mm Hg and thereafter carbon dioxide is again introduced into the mixture by the method described above. The newly formed β-napthol is distilled off and a third carboxylation is carried out. In total, 300 parts of carbon dioxide are absorbed in the course of 300 minutes' duration of carboxylation. The autoclave is then cooled and the reaction mixture is stirred with a solution of 90 parts of sodium hydroxide in 5,000 parts of water at from 95° to 100° C. The mixture is then acidified to about pH 6 with hydrochloric acid, whilst stirring vigorously. The β-naphthol which has separated out is filtered off at 30° C and the clear aqueous filtrate is acidified to pH 3 with hydrochloric acid (35% strength by weight) at from 85° to 90° C and stirred for a further 10 minutes. The resulting crystals of 2-hydroxy-naphthalene-3-carboxylic acid are filtered off and dried in vacuo at 70° C. 520 parts of end product (corresponding to 74% of theory, based on β-naphthol converted) are obtained. The proportion of resin formed is 11 mole percent, based on β-naphthol employed. 700 parts of β-naphthol are recovered.

EXAMPLE 2

An autoclave equipped with stirrer is charged with 1,220 parts of β-naphthol, 640 parts of aqueous sodium hydroxide solution (50% strength by weight) and 6 parts of the trisodium salt of nitrilotriacetic acid (dissolved in 15 parts of water). The charge is mixed thoroughly under nitrogen until the internal temperature reaches 260° C. 510 parts of 2-hydroxy-naphthalene-3-carboxylic acid (corresponding to 73% of theory, based on β-naphthol converted) are obtained analogously to Example 1. The proportion of resin formed is 12 mole percent, based on β-naphthol employed. 685 parts of β-naphthol are recovered.

EXAMPLE 3

An autoclave equipped with stirrer is charged with 1,260 parts of β-naphthol, 608 parts of aqueous sodium hydroxide solution (50% strength by weight), 27 parts of aqueous potassium hydroxide solution (85% strength by weight) and 36 parts of sodium hexametaphosphate (dissolved in 80 parts of water). The charge is mixed thoroughly under nitrogen and heated until the internal temperature reaches 260° C. The reaction is carried out analogously to Example 1 except that only one distillation of the β-naphthol liberated, between two carboxylation steps, is carried out. 530 parts of 2-hydroxy-naphthalene-3-carboxylic acid (corresponding to 75% of theory, based on β-naphthol converted) are obtained. The proportion of resin formed is 11 mole percent, based on β-naphthol employed. 715 parts of β-naphthol are recovered.

EXAMPLE 4

An autoclave equipped with stirrer is charged with 1,240 parts of β-naphthol, 608 parts of aqueous sodium hydroxide solution (50% strength by weight), 27 parts of aqueous potassium hydroxide solution (85% strength by weight) and 12 parts of the tetrasodium salt of ethylenediaminetetraacetic acid (dissolved in 50 parts of water). The charge is mixed thoroughly under nitrogen and heated until the internal temperature reaches 260° C. 520 parts of 2-hydroxy-naphthalene-3-carboxylic acid (corresponding to 74% of theory, based on β-naphthol converted) are obtained analogously to Example 1. The proportion of resin formed is 11 mole percent, based on β-naphthol employed. 700 parts of β-naphthol are recovered.

We claim:

1. A process for the manufacture of 2-hydroxy-naphthalene-3-carboxylic acid by reaction of sodium β-naphtholate with carbon dioxide at elevated temperatures, which comprises heating sodium β-naphtholate or a mixture of sodium β-naphtholate and potassium β-naphtholate in a first stage, in the presence of a catalytic amount of inhibitor selected from the group consisting of nitrogen compounds of the formula

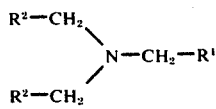

and polyphosphates containing at least 3 phosphorus atoms per molecule, wherein $R^1$ is carboxyl, metal carboxylate or the radical

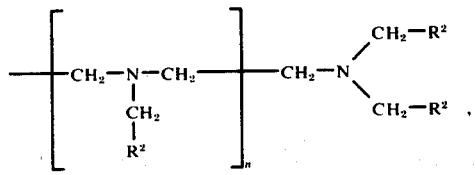

the radicals $R^2$ are identical or different and each is carboxyl, metal carboxylate or the radical —$CH_2OH$, $n$ is 0, 1 or 2, to a temperature of at least 180° C and reacting, in a second stage, said first stage reaction mixture with carbon dioxide at the above temperature, and the resulting salt of 2-hydroxy-naphthalene-3-carboxylic acid is then converted to 2-hydroxy-naphthalene-3-carboxylic acid by addition of an acid.

2. A process as set forth in claim 1, wherein the reaction is carried out with nitrogen compounds I and/or polyphosphates in an amount of from 0.001 to 0.1 mole per mole of the naphtholate starting material.

3. A process as set forth in claim 1, wherein the reaction is carried out with nitrogen compounds of the formula I, wherein $R^1$ is carboxyl, the radical

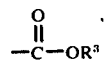

in which $R^3$ is a magnesium, calcium, sodium or potassium atom, or the radical

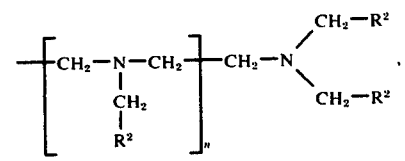

the radicals $R^2$ are identical or different and each is carboxyl, the radical

in which $R^3$ is a magnesium, calcium, sodium or potassium atom or the radical —$CH_2OH$ and $n$ is 0, 1 or 2, and/or polyphosphates containing at least 4 phosphorus atoms per molecule.

4. A process as set forth in claim 1, wherein the reaction is carried out with from 0.02 to 0.5 mole of potassium β-naphtholate per mole of sodium β-naphtholate.

5. A process as set forth in claim 1, wherein the reaction is carried out at from 200° to 280° C.

6. A process as set forth in claim 1, wherein the reaction is carried out at from 240° to 265° C.

7. A process as set forth in claim 1 wherein a mixture of nitrogen compounds of the formula I and polyphosphates is employed in the first stage.

* * * * *